United States Patent [19]

Sasaki et al.

[11] Patent Number: 5,528,362
[45] Date of Patent: Jun. 18, 1996

[54] ATOMIC ABSORPTION SPECTROPHOTOMETER FOR PROVIDING BACKGROUND CORRECTED ATOMIC ABSORBANCE-DATA

[75] Inventors: Kikuo Sasaki; Tomohiro Nakano, both of Kyoto, Japan

[73] Assignee: Shimadzu Corporation, Japan

[21] Appl. No.: 53,360

[22] Filed: Apr. 28, 1993

[30] Foreign Application Priority Data

Apr. 30, 1992 [JP] Japan .................. 4-139918

[51] Int. Cl.$^6$ ................................. G01J 3/36
[52] U.S. Cl. ............................. 356/307; 250/281
[58] Field of Search ........................ 356/307, 308, 356/346; 250/281, 288; 315/349

[56] References Cited

U.S. PATENT DOCUMENTS

| | | |
|---|---|---|
| 3,610,760 | 10/1971 | Lowe . |
| 4,462,685 | 7/1984 | Smith, Jr. et al. .............. 356/307 |
| 4,885,504 | 12/1989 | Green ............................. 313/618 |
| 4,979,823 | 12/1990 | Mohr et al. . |

FOREIGN PATENT DOCUMENTS

| | | |
|---|---|---|
| 0227038 | 7/1987 | European Pat. Off. . |
| 3837011 | 7/1989 | Germany . |
| 1190424 | 5/1970 | United Kingdom . |

*Primary Examiner*—F. L. Evans
*Assistant Examiner*—Robert Kim
*Attorney, Agent, or Firm*—Klima & Hopkins

[57] ABSTRACT

A lighting circuit part (26) is provided for lighting a hollow cathode lamp (1), to feed a large lighting current (I1) intermittently and periodically across an anode and a cathode by a control signal from a control part (22) while feeding a boost current (Ib) across a boost electrode and the anode in a part of a period when the lighting current (I1) flows across the anode and the cathode. Absorbance including both of atomic absorption of a sample and background absorption is detected with light emitted when the large current (I1) is fed across the anode and the cathode with feeding of the boost current (Ib) while absorbance by background absorption of the sample is detected with light emitted when the large current (I1) is fed across the anode and the cathode with no feeding of the boost current (Ib) so that difference between these absorbance levels is obtained to obtain true atomic absorption corrected as to background absorption. Thus, measurement is made in a high S-N ratio with background correction.

9 Claims, 5 Drawing Sheets

PROFILE IN PERIOD 2

PROFILE IN PERIOD 1

ATOMIC ABSORPTION SPECTROPHOTOMETER FOR PROVIDING BACKGROUND CORRECTED ATOMIC ABSORBANCE-DATA

BACKGROUND OF THE INVENTION

1. Field of the Invention

The present invention relates to a flame or flameless atomic absorption spectrophotometer, and more particularly, it relates to an atomic absorption spectrophotometer which performs background correction by a self-inversion system with a hollow cathode lamp employed as a light source.

2. Description of the Background Art

In a hollow cathode lamp, a hollow cylindrical cathode of a measured element and an anode of Ni or the like are loaded in a glass tube with a low-pressure filler gas, and a voltage is applied across the anode and the cathode so that free electrons collide with atoms of the filler gas to generate gas ions, which in turn are accelerated to collide with the cathode, thereby sputtering the cathode. The as-sputtered cathode atoms are excited through further collision with the gas ions, to emit a light of a characteristic spectrum of the cathode material.

Even if a lighting current is increased in order to obtain intense light in such a hollow cathode lamp, the light intensity is not necessarily increased. When the lighting current is increased, a large quantity of neutral atoms are generated in the cathode part to cause self- absorption of a resonance line. To this end, known is a hollow cathode lamp which is provided with a third electrode (boost electrode) to discharge neutral atoms thereby preventing self-absorption and increasing light intensity. Such a hollow cathode lamp provided with a boost electrode is described in U.S. Pat. No. 4,885,504, for example. The present invention utilizes such a hollow cathode lamp provided with a boost electrode as a light source.

In general, a hollow cathode lamp provided with a boost electrode is so employed that a current is regularly fed to the boost electrode to extract emissive light having strong light intensity. It is possible to perform spectroanalysis with an excellent S-N ratio, by increasing the emissive light in intensity and extracting a luminescent line having small self-absorption.

In an atomic absorption spectrophotometer employing a hollow cathode lamp provided with no boost electrode, a self-inversion method is carried out as one of background correction methods. In such a self-inversion method, absorbance measured with light which is emitted when a large current causing self-absorption is fed across an anode and a cathode is subtracted from that measured with light which is emitted when a small current is fed across the same, to carry out background correction. In this case, however, the result of measurement has an inferior S-N ratio due to weak radiant intensity for measuring atomic absorption.

An atomic absorption spectrophotometer employing such a self-inversion method is described in U.S. Pat. No. 4,462,685, for example.

SUMMARY OF THE INVENTION

An object of the present invention is to carry out measurement in a high S-N ratio using a hollow cathode lamp provided with a boost electrode, as well as to carry out background correction through the boost electrode.

According to the present invention, a current having a value causing self-absorption of a resonance line in a hollow cathode lamp is fed across an anode and a cathode to light the hollow cathode lamp, while a current is also fed across the boost electrode and the anode in a part of the lighting period. Measurement is so made that outputs of a detector are at least sampled in a period when the current flows across the boost electrode and the anode as well as the other current flows across the anode and the cathode and a period when the current flows only across the anode and cathode to obtain absorbance levels, and background-corrected atomic absorbance is calculated from the difference between the absorbance level obtained when the current flows across the boost electrode and the anode as well as the other current flows across the anode and the cathode and that obtained when the current flows only across the anode and the cathode.

When a large current is fed across the anode and the cathode, a large quantity of neutral atoms are generated in the cathode part to cause self-absorption of a resonance line, whereby the emissive light exhibits a spectrum which is reduced in light intensity at a resonance wavelength $\lambda r$, as shown at (F) in FIG. 4. When a large current is fed across the anode and the cathode while a current is also fed across the boost electrode and the anode, on the other hand, the neutral atoms generated in the cathode part are discharged, whereby the emissive light is increased in intensity at the resonance wavelength to exhibit a spectrum shown at (G) in FIG. 4. When absorbance of a sample is measured with light which is emitted when a large current is fed across the anode and cathode while a current is also fed across the boost electrode and the anode, obtained is data formed by both of atomic absorption by the sample and background absorption. When absorbance of the sample is measured with light which is emitted when a large current is fed across the anode and the cathode while no current is fed across the boost electrode and the anode, on the other hand, obtained is data mainly formed by background absorption of the sample. Consequently, it is possible to obtain true atomic absorption with correction of background absorption from the difference between the absorbance values.

When atomic absorbance is measured, a current is fed across the boost electrode and the anode to increase intensity of the emissive light at the resonance wavelength, whereby the data can be obtained in an excellent S-N ratio.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
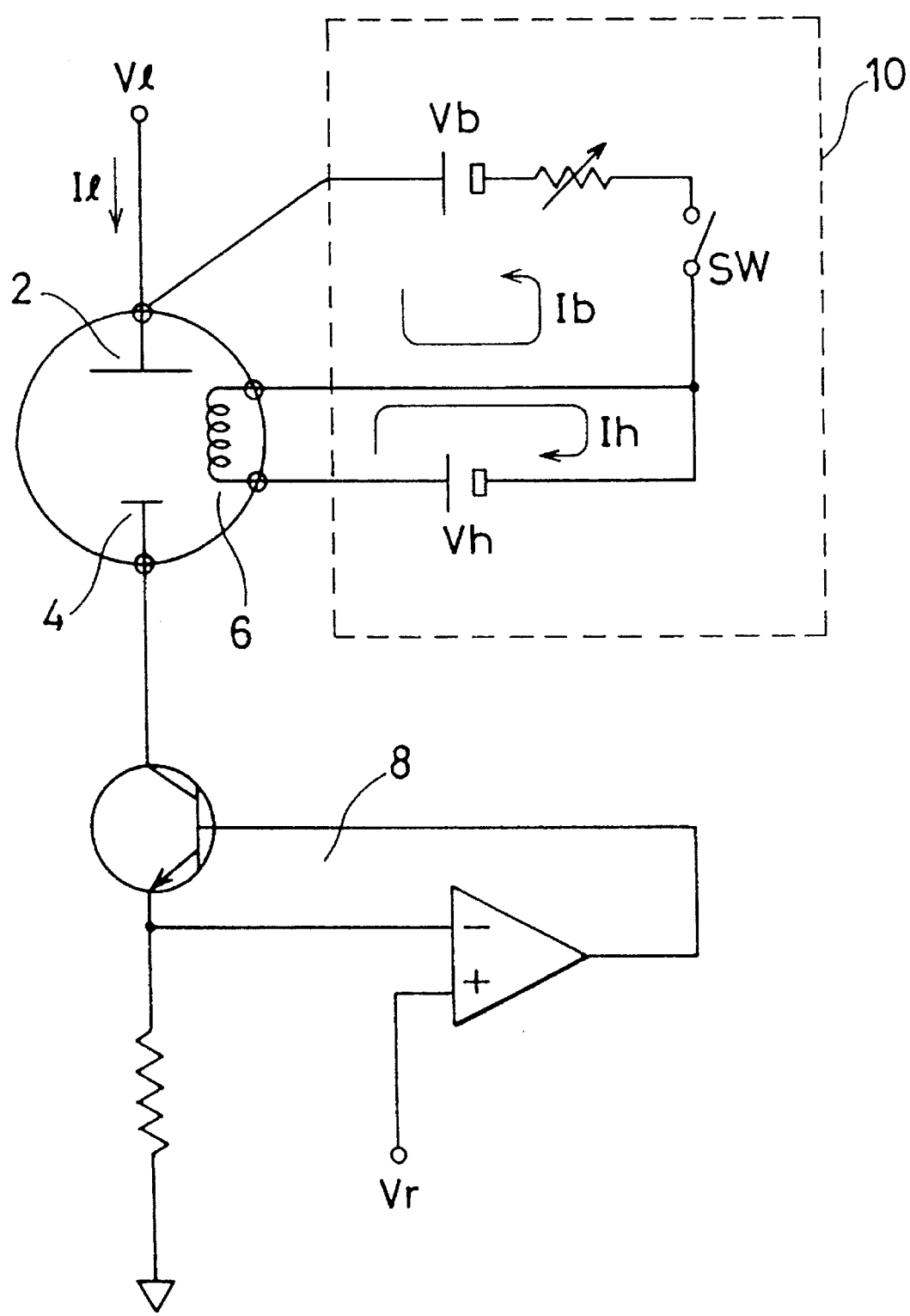
FIG. 1 is a circuit diagram showing a hollow cathode lamp employed in the present invention.

FIG. 1 illustrates a hollow cathode lamp which is employed in an embodiment of the present invention and a lighting circuit part thereof.

An anode 2, a cathode 4 and a boost electrode 6 are loaded in a glass tube with a low-pressure filler gas. The cathode 4 is connected with a constant current circuit 8, so that a constant current I1 flows across the anode 2 and the cathode 4. This current I1 is set at several 100 mA, so that emission intensity at a resonance wavelength λr is reduced in an emission profile obtained with this current when no current flows across the boost electrode 6 and the anode 2, as shown at (F) in FIG. 4. The boost electrode 6 is connected with a boost electrode power supply part 10, which feeds a base electrode Ih by a power source Vh while feeding a boost current Ib across the boost electrode 6 and the anode 2.

Figure 2:
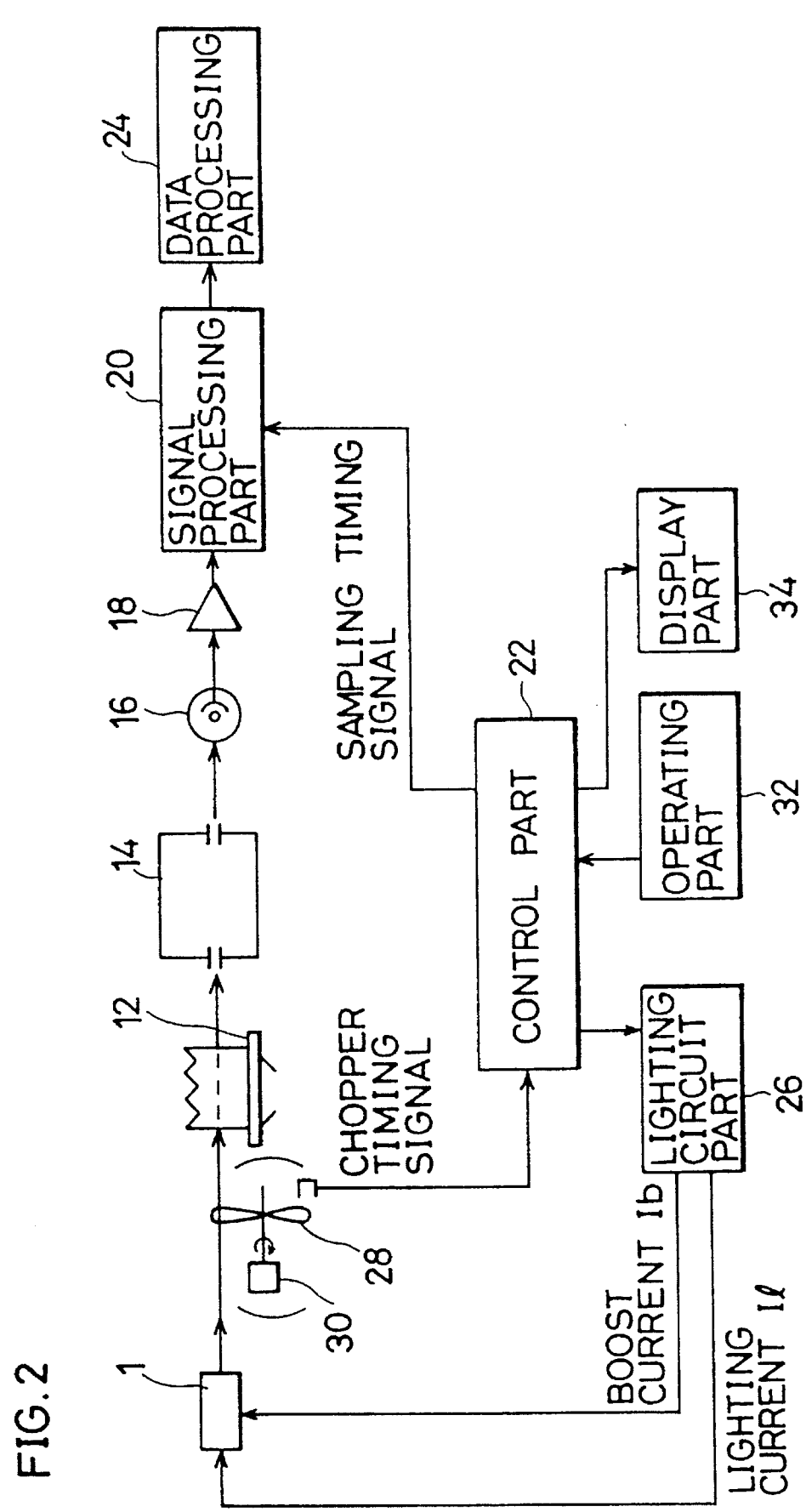
FIG. 2 is a block diagram showing an atomic absorption spectrophotometer according to an embodiment of the present invention.

FIG. 2 illustrates an exemplary atomic absorption spectrophotometer, which comprises the hollow cathode lamp 1 shown in FIG. 1 as a light source. Light which is emitted from the hollow cathode lamp 1 is passed through an atomization part 12 for atomizing a sample. The emissive light which is passed through the atomization part 12 is spectroscopically analyzed by a spectroscope 14, and detected by a detector 16. A detection signal outputted from the detector 16 is amplified by a preamplifier 18 and then sampled in a signal processing part 20 along a sampling timing signal received from a control part 22, so that background-corrected absorbance is obtained and transmitted to a data processing part 24. A lighting circuit part 26, which is adapted to light the hollow cathode lamp 1, feeds a lighting current I1 across the anode 2 and the cathode 4 while feeding a boost current Ib across the boost electrode 6 and the anode 2. In order to intermittently and periodically pass the emissive light from the hollow cathode lamp 1 through the atomization part 12, the control part 22 controls the lighting circuit part 26 to intermittently and periodically feed the lighting current I1 and the boost current Ib while controlling the sampling timing at the signal processing part 20 according to this embodiment.

In another embodiment of the present invention, on the other hand, a lighting current I1 is fed continuously and a chopper 28 which is driven by a motor 30 is adapted to intermit the optical path. The control part 22 incorporates a driving signal for the chopper 28 as a timing signal, to control the timing for feeding the boost current Ib and the sampling timing at the signal processing part 20. The control part 22 is also connected with an operating part 32 and a display part 34.

Figure 3:
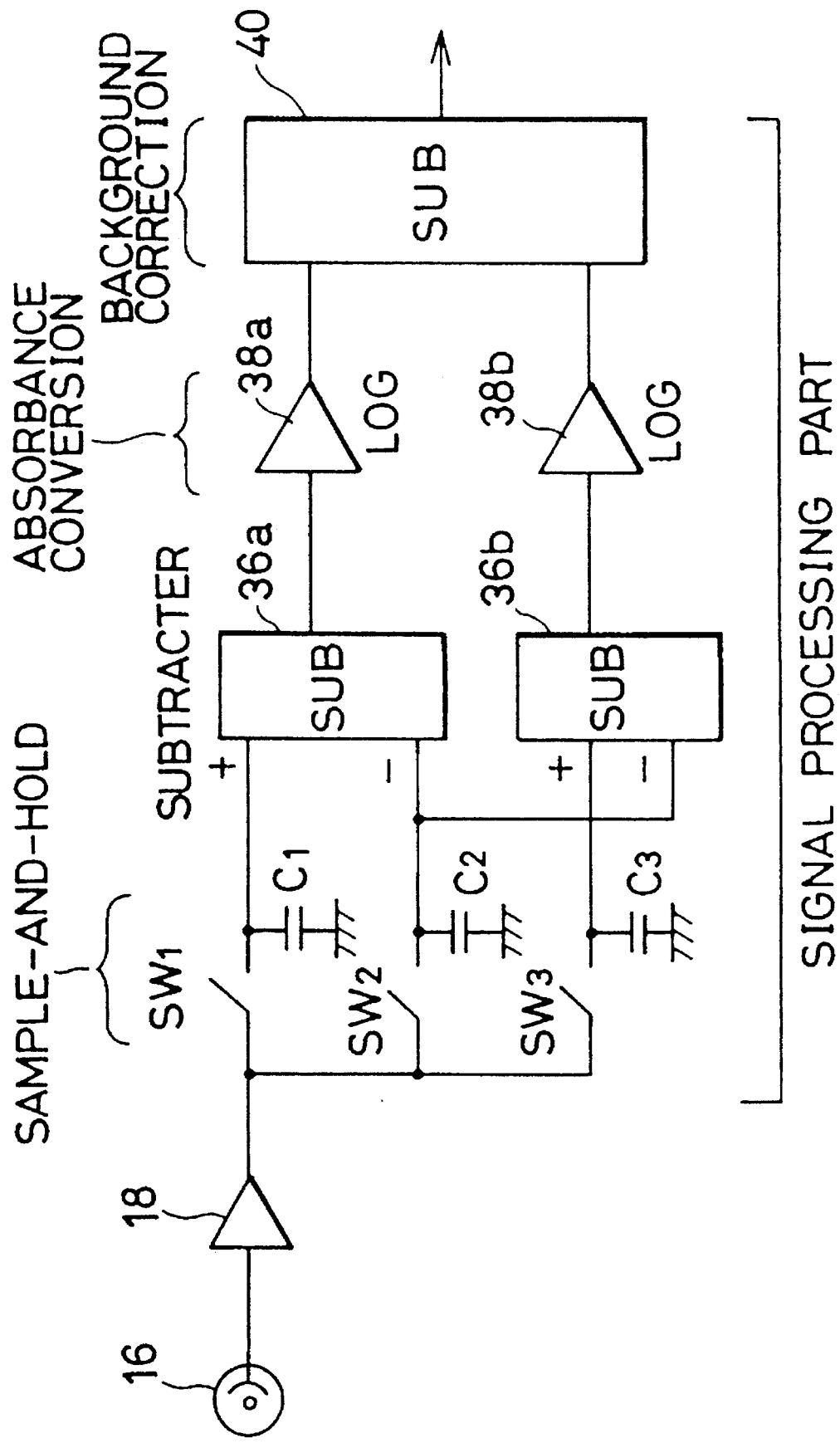
FIG. 3 is a circuit diagram showing an exemplary signal processing part provided in the embodiment.
Figure 4A:
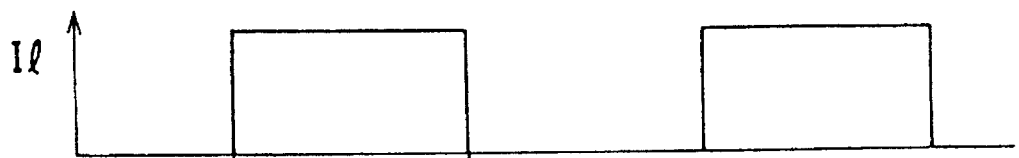
FIG. 4 illustrates waveform diagrams showing the operation timings of the embodiment and light emission profiles of the hollow cathode lamp at respective timings.
Figure 4B:
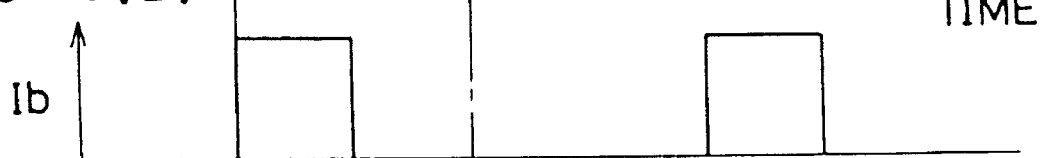
Figure 4C:
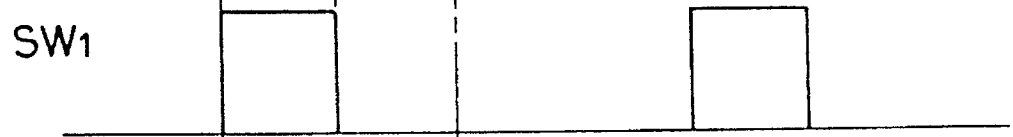
Figure 4D:
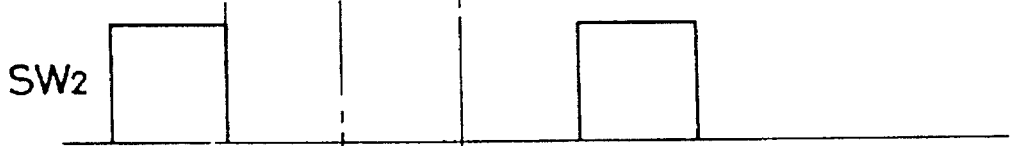
Figure 4E:
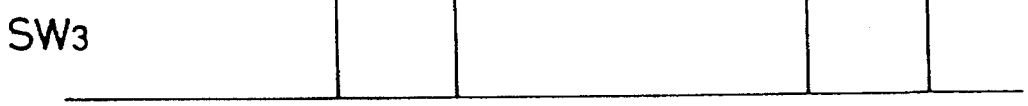
Figure 4F:
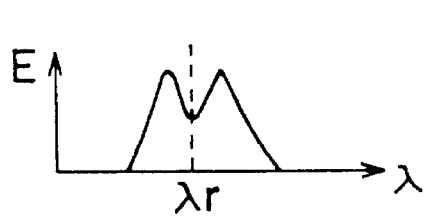
Figure 4G:
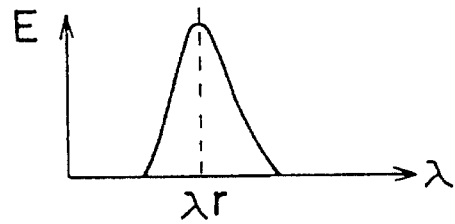

FIG. 3 illustrates an exemplary signal processing part 20 of the embodiment shown in FIG. 2. In a sample-and-hold circuit comprising switches $SW_1$ to $SW_3$ and capacitances $C_1$ to $C_3$, the switches $SW_1$ to $SW_3$ are on-off controlled by the sampling timing signal received from the control part 22, to incorporate the signal which is outputted from the detector 16 and amplified by the preamplifier 18. The first switch $SW_1$ is adapted to sample a value of the sample which is measured when the current I1 is fed across the anode 2 and cathode 4 of the hollow cathode lamp 1 with the boost current Ib to ensure large emissive light at the resonance wavelength, the third switch $SW_3$ is adapted to sample data at a timing when the large current I1 is fed only across the anode 2 and cathode 4 to mainly measure background absorption, and the second switch $SW_2$ is adapted to sample a base level signal at a timing when no emissive light from the light source 1 is passed through the atomization part 12.

A first subtracter 36a is adapted to subtract the base level from a signal including atomic absorption and background absorption, and a second subtracter 36b is adapted to subtract the base level from the background absorption. Numeral 38a denotes a LOG amplifier (first conversion amplifier) for converting an output from the subtracter 36a to absorbance, and numeral 38b denotes an LOG amplifier (second conversion amplifier) for converting an output from the subtracter 36b to absorbance. A third subtracter 40 is adapted to calculate difference between absorbance values received from the LOG amplifiers 38a and 38b for obtaining background-corrected atomic absorption. An output of the subtracter 40 is transmitted to the data processing part 24 or the display part 34.

The operation of this embodiment is now described with reference to FIG. 4. The current I1 is intermittently and periodically fed across the anode 2 and the cathode 4 of the hollow cathode lamp 1 at the timing shown at (A). The boost current Ib is fed across the boost electrode 6 and the anode 2 at the timing shown at (B). The boost current Ib, which is fed in a part of a period ① when the current I1 flows across the anode 2 and the cathode 4, may be fed in any of first and second halves and an intermediate part of the said period ①. In the example shown in FIG. 4, the boost current Ib is fed in a first half of the period ① when the current I1 flows across the anode 2 and the cathode 4.

An emission profile obtained in the period ① when the boost current Ib flows in the hollow cathode lamp 1 has strong emission intensity at the resonance wavelength *r as shown at (G), while such emission intensity at the resonance wavelength λr is reduced by self-absorption in an emission period ② when no boost current Ib flows in the hollow cathode lamp 1.

The switch $SW_1$ shown in FIG. 3 is turned on in the period ①, so that both of atomic absorption and background absorption of the sample are detected by the emissive light from the light source 1 having strong emission intensity at the resonance wavelength λr. On the other hand, the switch $SW_3$ is turned on in the period ②, so that the background absorption is mainly detected. Further, the switch $SW_2$ is turned on at a timing when the light source 1 emits no light, so that the base level signal is detected.

In the embodiment shown in FIGS. 1 and 2, the lighting circuit part 26 is controlled by the control signal received from the control part 22 to light the light source 1 in order to intermittently and periodically pass the emissive light through the atomization part 12. Alternatively, the chopper 28 may be provided to intermit the optical path, thereby intermittently and periodically passing measuring light through the atomization part 12.

Figure 5:
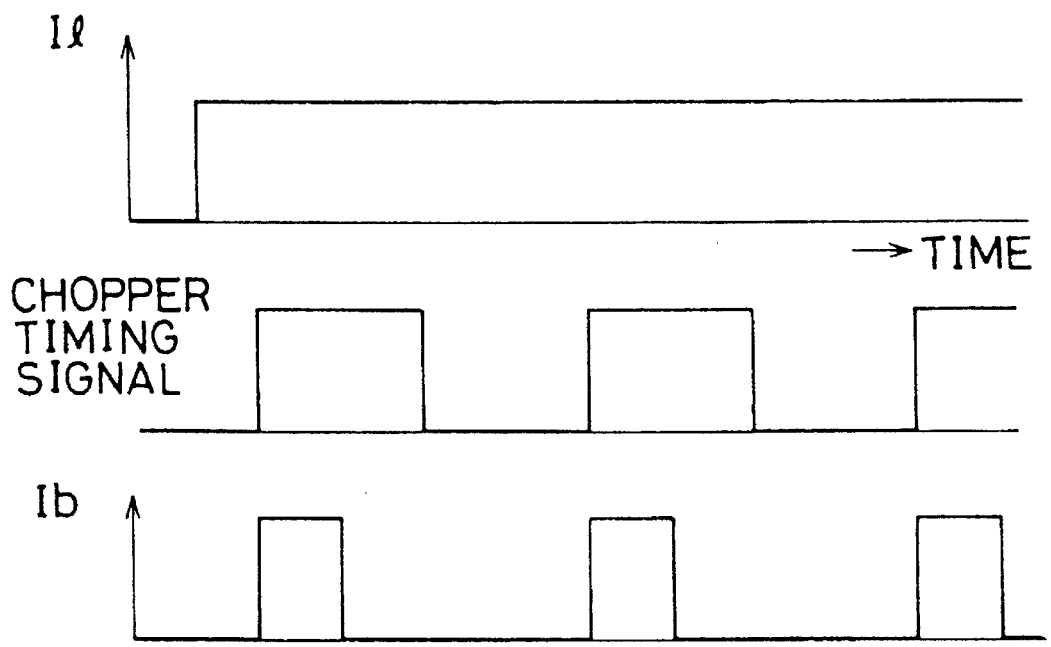
FIG. 5 is a waveform diagram showing operation timings in another embodiment of the present invention.

When the chopper 28 is employed, an emission current I1 is continuously fed across the anode 2 and the cathode 4 as shown in FIG. 5, so that the measuring light is intermittently and periodically passed to the atomization part 12 by the chopper 28. In this case, the control part 22 controls the lighting circuit part 26 on the basis of the chopper timing signal so that the boost current Ib is fed across the boost electrode 6 and the anode 2 in a part of a period when the measuring light is passed through the atomization part 12. The sampling timings at the signal processing part 20 are identical to those described above with reference to FIG. 4.

Also when the chopper 28 is employed, the boost current Ib may be fed in any of first and second halves and an intermediate part of the period when the light from the light source 1 is passed through the atomization part 12.

This chopper 28 may be arranged on any position of the optical path between the hollow cathode lamp 1 and the detector 16.

Figure 6:
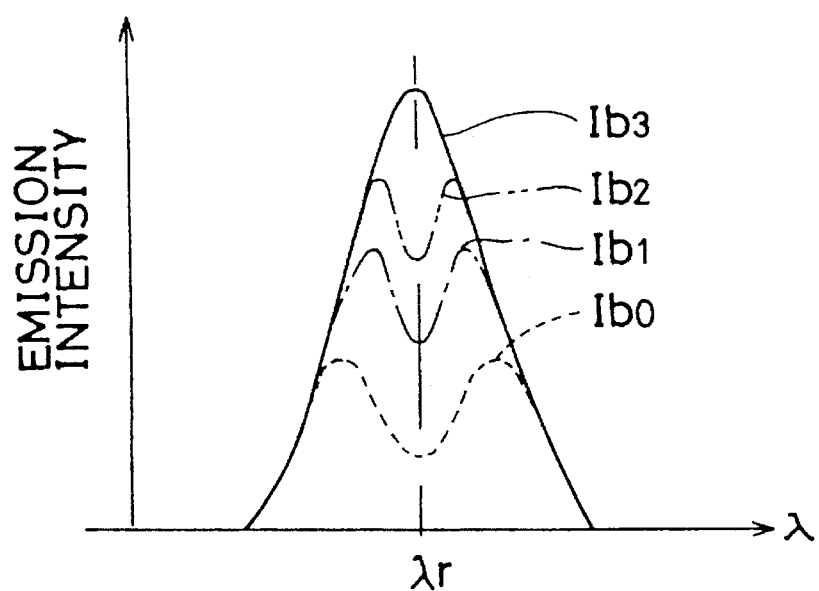
FIG. 6 illustrates emission profiles for changing detection sensitivity.

When a current causing self-absorption is fed across an anode and a cathode of a hollow cathode lamp, it is possible to prevent such self-absorption by feeding a boost current. In this case, the degree of prevention of self-absorption is varied with the level of the boost current, such that emission intensity at a resonance wavelength $\lambda r$ is increased upon increase of the boost current. In an emission profile shown in FIG. 6, strong emission intensity is attained at the resonance wavelength $\lambda r$ with a sufficient boost current level $Ib_3$, while such emission intensity at the resonance wavelength $\lambda r$ is reduced as the boost current is reduced as $Ib_2$ and $Ib_1$. To this end, it is possible to change atomic absorption sensitivity in execution of background correction by employing emissive light with zero boost current ($Ib_0$) for measuring background absorption and feeding a boost current for measurement including atomic absorption and background absorption while varying the boost current as $Ib_3$, $Ib_2$ and $Ib_1$. In other words, it is possible to increase atomic absorption sensitivity by increasing the boost current thereby increasing emission intensity at the resonance wavelength $\lambda r$, while it is possible to reduce atomic absorption sensitivity by reducing the boost current. Thus, it is possible to change detection sensitivity in response to sample concentration by changing the boost current $Ib$ along the control signal from the control part 22, thereby widening the dynamic range.

In the method of changing detection sensitivity, the boost electrode power supply part 10 shown in FIG. 1 may be adapted to change the base current $Ih$. In this case, it is possible to increase self-absorption by increasing the base current $Ih$ in a state feeding the boost current $Ib$, thereby reducing detection sensitivity.

While the embodiment has been described with reference to a flame atomic absorption spectrophotometer, the present invention is also applicable to an atomic absorption spectrophotometer having a flameless atomization part.

According to the present invention, the hollow cathode lamp is provided with a boost electrode, so that a current fed to the boost electrode is intermitted for measuring absorbance. The boost current is so fed as to suppress self-absorption at the resonance wavelength while atomic absorption is measured in a high S-N ratio with measuring light of strong emission intensity, thereby obtaining background-corrected absorbance from difference between absorbance levels measured with feeding and no feeding of the boost current. Consequently, it is possible to perform background-corrected measurement in a high S-N ratio according to the present invention.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An atomic absorption spectrophotometer, comprising:
   a hollow cathode lamp serving as a light source, said hollow cathode lamp comprising an anode, a cathode, and a third electrode arranged so that current is fed across said third electrode and said anode for discharging neutral atoms:
   an atomization part for atomizing a sample and receiving measuring light being transmitted from said hollow cathode lamp through the atomized sample;
   a spectroscope for spectroscopically analyzing said measuring light being transmitted through said atomization part;
   a detector for detecting the measuring light spectroscopically analyzed by said spectroscope;
   a lighting circuit part for lighting said hollow cathode lamp;
   a signal processing part for obtaining absorbance from a detection signal received from said detector;
   a control part for controlling lighting of said hollow cathode lamp and data sampling of said signal processing part
   wherein said control part controls said lighting circuit part to intermittently feed a current of a level causing self-absorption of a resonance line in said hollow cathode lamp across said anode and said cathode for lighting said hollow cathode lamp and to feed a current across said third electrode and said anode in part of a lighting period while controlling said signal processing part to sample at least outputs of said detector in a period when a current flows across said anode and said cathode as well as another current flows across said third electrode and said anode and a period when a current flows only across said anode and said cathode, and
   a signal processing part calculates background-corrected atomic absorbance from a difference between absorbance levels in said period when a current flows across said anode and said cathode as well as another current flows across said third electrode and said anode and said period when a current flows only across said anode and said cathode.

2. An atomic absorption spectrophotometer in accordance with claim 1, wherein
   said lighting circuit part comprises:
   a constant current circuit for feeding a constant current across said anode and said cathode, and
   a power supply part including a switch for intermitting a current being fed across said third electrode and said anode.

3. An atomic absorption spectrophotometer in accordance with claim 1, wherein
   said control part controls said signal processing part to sample an output of said detector also in a period when no current flows across said anode and said cathode of said hollow cathode lamp.

4. An atomic absorption spectrophotometer in accordance with claim 1, wherein
   said signal processing part comprises:
   a first sample-and-hold circuit including a first switch for sampling a detection signal obtained when a current flows across said anode and said cathode of said hollow cathode lamp as well as another current flows across said third electrode and said anode while measuring light is incident upon said detector,
   a second sample-and-hold circuit including a second switch for sampling a detection signal obtained when no measuring light is incident upon said detector,
   a third sample-and-hold circuit including a third switch for sampling a detection signal obtained when a current flows across said anode and said cathode of said hollow cathode lamp and no current flows across said third electrode and said anode while measuring light is incident upon said detector,
   a first subtracter for calculating difference between output signals of said first and second sample-and-hold circuits,
   a second subtracter for calculating difference between output signals of said third and second sample-and-hold circuits, a first conversion amplifier for converting an output of said first subtracter to absorbance, a second conversion amplifier for converting an output of said second subtracter to absorbance, and a third subtracter for calculating difference between absorbance outputs from said first and second conversion amplifiers for outputting background-corrected absorbance.

5. An atomic absorption spectrophotometer in accordance with claim 1, further comprising means for making the value of a current flowing across said third electrode and said anode variable between a value for effectively preventing self-absorption of a resonance line and zero, thereby changing atomic absorption sensitivity.

6. An atomic absorption spectrophotometer in accordance with claim 5, wherein the value of said current flowing across said third electrode and said anode is changed by a control signal from said control part.

7. An atomic absorption spectrophotometer in accordance with claim 1, further comprising means for making a base current value of said third electrode variable, thereby changing atomic absorption sensitivity.

8. An atomic absorption spectrophotometer, comprising:

a hollow cathode lamp serving as a light source, said hollow cathode lamp comprises an anode and a cathode as well as a third electrode so that a current is fed across said third electrode and said anode for discharging neutral atoms;

an atomization part for atomizing a sample and receiving measuring light being transmitted from said hollow cathode lamp through the atomized sample;

a spectroscope for spectroscopically analyzing said measuring light being transmitted through said atomization part;

a detector for detecting said measuring light spectroscopically analyzed by said spectroscope;

a lighting circuit part for lighting said hollow cathode lamp;

a signal processing part for obtaining absorbance from a detection signal received from said detector;

a control part for controlling lighting of said hollow cathode lamp and data sampling of said signal processing part; and a chopper provided at a position for intermitting an optical path between said hollow cathode lamp and said detector, wherein a lighting current flowing across said anode and said cathode of said hollow cathode lamp is controlled to continuously flow, and a period when a current flows across said third electrode and said anode is controlled on the basis of a timing signal for controlling an operation of said chopper to form a part of a period when measuring light incident upon said detector.

9. An atomic absorption spectrophotometer in accordance with claim 8, wherein said signal processing part comprises:

a first sample-and-hold circuit including a first switch for sampling a detection signal obtained when a current flows across said anode and said cathode of said hollow cathode lamp as well as another current flows across said third electrode and said anode while measuring light incident upon said detector;

a second sample-and-hold circuit including a second switch for sampling a detection signal obtained when no measuring light is incident upon said detector;

a third sample-and-hold circuit including a third switch for sampling a detection signal obtained when a current flows across said anode and said cathode of said hollow cathode lamp and no current flows across said third electrode and said anode while measuring light is incident upon said detector;

a first subtracter for calculating a difference between output signals of said first and second sample-and-hold circuits;

a second subtracter for calculating a difference between output signals of said third and second sample-and-hold circuits;

a first conversion amplifier for converting an output of said first substracter to absorbance;

a second conversion amplifier for converting an output of said second subtracter to absorbance, and a third substracter for calculating a difference between absorbance outputs from said first and second conversion amplifiers for outputting background-corrected absorbance.

* * * * *